US010501697B2

(12) United States Patent
Scott

(10) Patent No.: US 10,501,697 B2
(45) Date of Patent: Dec. 10, 2019

(54) BIODIESEL COMPOSITION AND RELATED PROCESS AND PRODUCTS

(71) Applicants: Argent Energy (UK) Limited, North Lanarkshire (GB); Argent Energy Limited, London (GB)

(72) Inventor: Michael Scott, Motherwell (GB)

(73) Assignees: Argent Energy (UK) Limited, North Lanarkshire (GB); Argent Energy Limited, London (GB)

( * ) Notice: Subject to any disclaimer, the term of this patent is extended or adjusted under 35 U.S.C. 154(b) by 0 days.

(21) Appl. No.: 15/699,393

(22) Filed: Sep. 8, 2017

(65) Prior Publication Data

US 2017/0369803 A1    Dec. 28, 2017

Related U.S. Application Data

(63) Continuation of application No. 14/898,004, filed as application No. PCT/GB2014/051877 on Jun. 19, 2014, now Pat. No. 9,868,918.

(30) Foreign Application Priority Data

Jun. 19, 2013 (GB) .................................. 1310960.8
Jun. 19, 2013 (GB) .................................. 1310961.6
Jun. 19, 2013 (GB) .................................. 1310962.4

(51) Int. Cl.
    *C10L 1/00*       (2006.01)
    *C10L 1/02*       (2006.01)
    (Continued)

(52) U.S. Cl.
    CPC .............. *C10L 1/026* (2013.01); *C07C 67/03* (2013.01); *C07C 67/08* (2013.01); *C07C 67/58* (2013.01);
    (Continued)

(58) Field of Classification Search
    CPC ................. C10L 1/026; C10L 2290/18; C10L 2290/542; C10L 2200/0446; C10L 2200/0476; C10L 2270/04; C10L 2290/06; C10L 2290/544; C10L 2290/547; C10L 2270/026; C10L 2290/543; C10G 3/00; C10G 3/40; C10G 2300/1003; C10G 2300/201; C10G 2400/04; C07C 67/03; C07C 67/08; C07C 67/58; C11B 3/001; C11B 3/006; C11B 3/008; C11B 3/16;
    (Continued)

(56) References Cited

U.S. PATENT DOCUMENTS

| 8,613,780 B2* | 12/2013 | Asthana ................. C10L 1/026 44/388 |
| 2004/0231236 A1* | 11/2004 | May ......................... C10L 1/19 44/401 |
| 2011/0192076 A1 | 8/2011 | Hess et al. |

FOREIGN PATENT DOCUMENTS

| CN | 102492494 | * | 6/2012 |
| CN | 102492494 A | | 6/2012 |

(Continued)

*Primary Examiner* — Cephia D Toomer
(74) *Attorney, Agent, or Firm* — Dorton & Willis LLP; Ryan Willis

(57) ABSTRACT

There is described a biodiesel composition and process for producing biodiesel and related products. There is also described related fuels and fuel blends comprising biodiesel. The biodiesel composition may be prepared from a mixture comprising fats, oils and greases from sewer waste.

21 Claims, 4 Drawing Sheets

(51) Int. Cl.
*C10G 33/00* (2006.01)
*C10G 3/00* (2006.01)
*C07C 67/03* (2006.01)
*C07C 67/08* (2006.01)
*C07C 67/58* (2006.01)
*C11B 3/00* (2006.01)
*C11B 3/16* (2006.01)
*C11C 3/00* (2006.01)
*C11B 3/04* (2006.01)
*C11B 3/12* (2006.01)
*C11C 3/10* (2006.01)
*B01D 21/26* (2006.01)
*B03D 1/14* (2006.01)

(52) U.S. Cl.
CPC ............... *C10G 3/00* (2013.01); *C10G 3/40* (2013.01); *C10G 33/00* (2013.01); *C11B 3/001* (2013.01); *C11B 3/006* (2013.01); *C11B 3/008* (2013.01); *C11B 3/04* (2013.01); *C11B 3/12* (2013.01); *C11B 3/16* (2013.01); *C11C 3/003* (2013.01); *C11C 3/10* (2013.01); *B01D 21/262* (2013.01); *B03D 1/1431* (2013.01); *C10G 2300/1003* (2013.01); *C10G 2300/201* (2013.01); *C10G 2400/04* (2013.01); *C10L 2200/0446* (2013.01); *C10L 2200/0476* (2013.01); *C10L 2270/026* (2013.01); *C10L 2270/04* (2013.01); *C10L 2290/06* (2013.01); *C10L 2290/18* (2013.01); *C10L 2290/542* (2013.01); *C10L 2290/543* (2013.01); *C10L 2290/544* (2013.01); *C10L 2290/547* (2013.01); *Y02E 50/13* (2013.01); *Y02P 30/20* (2015.11)

(58) Field of Classification Search
CPC ... C11B 3/04; C11B 3/12; C11C 3/003; Y02E 50/13; Y02P 30/20; B01D 21/262; B03D 1/1431
See application file for complete search history.

(56) References Cited

FOREIGN PATENT DOCUMENTS

| CN | 102585927 A | 7/2012 |
| WO | WO2004083350 A1 | 9/2004 |
| WO | WO2010043213 A1 | 4/2010 |
| WO | 2014202981 A1 | 6/2015 |

\* cited by examiner

BIODIESEL COMPOSITION AND RELATED PROCESS AND PRODUCTS

CROSS REFERENCE TO RELATED APPLICATIONS

The present application is a continuation of U.S. patent application Ser. No. 14/898,004, filed Dec. 11, 2015 and titled, "BIODIESEL COMPOSITION AND RELATED PROCESS AND PRODUCTS," which is a national stage application of PCT/GB14/51877, filed Jun. 19, 2014, titled, "BIODIESEL COMPOSITION AND RELATED PROCESS AND PRODUCTS, which claimed priority under 35 U.S.C. § 119 to United Kingdom patent application serial numbers 1310960.8, 1310961.6, and 1310962.4, all filed on Jun. 19, 2013, the disclosures of each of the foregoing are incorporated herein by reference.

FIELD OF THE INVENTION

This invention relates to a biodiesel composition and process for producing biodiesel and related products. The invention also relates to fuels and fuel blends comprising biodiesel. In particular, the invention relates to a biodiesel composition prepared from a mixture comprising fats, oils and greases from sewer waste.

BACKGROUND OF THE INVENTION

The term "biodiesel" is used to refer to vegetable or animal fat, oil or grease derived diesel, consisting of long-chain alkyl methyl (ethyl or propyl) esters. Biodiesel is distinct from petroleum diesel (also known as petrodiesel or petroleum derived diesel), which is a specific fractional distillate of petroleum fuel oil. Biodiesel is typically produced from a variety of feedstocks, including edible and non-edible fats and oils.

Fats are triglycerides (triesters of glycerol and any of several fatty acids), and may be either solid or liquid at room temperature. Oils are neutral, non-polar molecules with a high hydrocarbon content. Greases are semisolid lubricants which generally consist of a soap emulsified with mineral or vegetable oil. Greases can be of natural origin, and can be either vegetable or animal derived.

Many biodiesel feedstock fats and oils have high purity, and therefore can be easily converted to biodiesel in a predictable way using known processes and known reaction conditions. However, in general pure feedstocks are more costly, the feedstocks having other potential uses.

There is also available a variety of poor quality and less pure sources of fats and oils (and greases), which can potentially be used to produce biodiesel. However, impure feedstocks are generally more problematic, leading to unpredictable reaction conditions and a less pure, less predictable biodiesel product. One such potential feedstock is the fats, oils and greases which are constituents of sewer waste or sewage, in which context they are referred to commonly as "sewer grease".

Fats, oils and greases gather in sewer waste and are very problematic, leading to the blockage of sewerage systems. Thus they are generally considered a problematic waste product. Nevertheless, such fats, oils and greases do contain hydrocarbons, which are a potential source of valuable products such as, for example, fuels.

Typically, however, sewer grease comprises a number of waste products and aqueous materials. For example, sewer grease contains a large amount of insoluble debris and many different chemicals. Furthermore, sewer grease is very viscous and has a relatively high melting point, which is why it causes sewerage systems to become blocked.

Fuels are required to have a certain degree of purity in order to be usable. For example, biodiesel needs to have a certain purity or FAME (fatty acid methyl ester) value in order to be usable in engines or the like. Current legislation (EN 14214) states that in order to be suitable for use in engines, biodiesel must have a minimum ester content of 96.5%. Furthermore, in order to be usable in modern engines, fuels must have an acceptable cetane number. Cetane number is a measurement of the combustion quality of diesel fuel during compression ignition. It is a significant expression of the quality of a diesel fuel. A higher cetane number is ordinarily more desirable as this indicates that a fuel will more easily combust in a diesel engine, giving a smoother (and sometimes more efficient) engine.

In general, the starting material used has a large impact on the quality of the biodiesel obtained, and FAME and the cetane number. In particular, low quality starting materials are normally associated with fuels having low FAME and low cetane number. A number of other measurements determine overall diesel fuel quality including: density, lubricity, cold-flow properties (cold filter plugging point), monoglyceride content, and sulphur content. These measurements are also typically affected by the quality of the starting material used.

Therefore, due to the impure and unpredictable nature of sewer grease, it has not been practicable to use sewer grease as a source of fats, oils and greases for producing fuels such as biodiesel.

It is an object of the present invention to overcome or mitigate at least some of the problems of the prior art.

SUMMARY OF THE INVENTION

According to a first aspect of the invention, there is provided a biodiesel composition comprising a mixture of esters, wherein the ester mixture comprises from about 7% by weight to about 10.5% by weight methyl octadecanoate (stearic acid methyl ester/methyl stearate).

The ester mixture may comprise from about 0.5% by weight to about 1.9% by weight methyl heptadecanoate (heptadecanoic acid methyl ester/methyl margarate).

The ester mixture may comprise from about 2.4% by weight to about 2.9% by weight methyl tetradecanoate (myristic acid methyl ester/methyl myristate).

The ester mixture may comprise from about 22.7% by weight to about 24.4% by weight methyl hexadecanoate (palmitic acid methyl ester/methyl palmitate).

The ester mixture may comprise from about 1.5% by weight to about 2.1% by weight methyl cis-9-hexadecenoate (palmitoleic acid methyl ester/methyl palmitoleate).

The ester mixture may comprise from about 39% by weight to about 41% by weight methyl cis-9-octadecenoate (oleic acid methyl ester/methyl oleate).

The ester mixture may comprise from about 15% by weight to about 20% by weight methyl cis,cis-9,12-octadecadienoate (linoleic acid methyl ester/methyl linoleate). Optionally the ester mixture comprises from about 18% by weight to about 20% by weight methyl cis,cis-9,12-octadecadienoate (linoleic acid methyl ester/methyl linoleate). Optionally the ester mixture comprises from more than about 18% by weight to about 20% by weight methyl cis,cis-9,12-octadecadienoate (linoleic acid methyl ester/methyl linoleate). Optionally the ester mixture comprises from more than about 19% by weight to about 20% by weight methyl cis,cis-9,12-octadecadienoate (linoleic acid methyl ester/methyl linoleate).

The ester mixture may comprise from about 2% by weight to about 3% by weight methyl cis,cis,cis-9,12,15-octadecatrienoate (linolenic acid methyl ester/methyl linolenate).

The ester mixture may comprise from about 0.17% by weight to about 0.2% by weight methyl eicosanoate (arachidic acid methyl ester/methyl arachidate).

The ester mixture may comprise from about 0.4% by weight to about 0.6% by weight methyl cis-9-eicosenoate (gadoleic acid methyl ester/methyl gadoleate).

The ester mixture may comprise from about 0.03% by weight to about 0.07% by weight methyl docosanoate (behenic acid methyl ester/methyl behenate).

The ester mixture may comprise from about 0.04% by weight to about 0.07% by weight methyl cis-13-docosenoate (erucic acid methyl ester/methyl erucate).

The ester mixture may comprise from about 0.28% by weight to about 0.3% by weight methyl tetracosanoate (lignoceric acid methyl ester/methyl lignocerate).

The ester mixture may comprise from about 0.04% by weight to about 0.08% by weight methyl cis-15-tetracosenoate (nervonic acid methyl ester/methyl nervonate).

The composition may comprise a cetane number of from about 60 to about 65.

The composition may comprise a cold filter plugging point of from about 1° C. to about 5° C.

The composition may comprise a density of from about 865 kgm$^{-3}$ to about 875 kgm$^{-3}$.

The esters may be alkyl esters, optionally mono-alkyl esters, optionally methyl esters.

The biodiesel composition may be obtained from a mixture comprising fat, oil and/or grease. The fat, oil and/or grease may be obtained from sewage.

The composition may comprise from about 98% by weight to about 99% by weight ester mixture.

According to a second aspect of the invention there is provided a fuel comprising the biodiesel composition of the first aspect.

According to a third aspect of the invention there is provided a fuel blend comprising the biodiesel composition of the first aspect, and a petroleum diesel.

According to a fourth aspect of the invention there is provided a biodiesel composition comprising a mixture of esters, wherein the ester mixture comprises from about 0.5% by weight to about 1.9% by weight methyl heptadecanoate (heptadecanoic acid methyl ester/methyl margarate).

The ester mixture may comprise from about 7% by weight to about 10.5% by weight methyl octadecanoate (stearic acid methyl ester/methyl stearate).

The ester mixture may comprise from about 2.4% by weight to about 2.9% by weight methyl tetradecanoate (myristic acid methyl ester/methyl myristate).

The ester mixture may comprise from about 22.7% by weight to about 24.4% by weight methyl hexadecanoate (palmitic acid methyl ester/methyl palmitate).

The ester mixture may comprise from about 1.5% by weight to about 2.1% by weight methyl cis-9-hexadecenoate (palmitoleic acid methyl ester/methyl palmitoleate).

The ester mixture may comprise from about 39% by weight to about 41% by weight methyl cis-9-octadecenoate (oleic acid methyl ester/methyl oleate).

The ester mixture may comprise from about 15% by weight to about 20% by weight methyl cis,cis-9,12-octadecadienoate (linoleic acid methyl ester/methyl linoleate). Optionally the ester mixture comprises from about 18% by weight to about 20% by weight methyl cis,cis-9,12-octadecadienoate (linoleic acid methyl ester/methyl linoleate). Optionally the ester mixture comprises from more than about 18% by weight to about 20% by weight methyl cis,cis-9,12-octadecadienoate (linoleic acid methyl ester/methyl linoleate). Optionally the ester mixture comprises from more than about 19% by weight to about 20% by weight methyl cis,cis-9,12-octadecadienoate (linoleic acid methyl ester/methyl linoleate).

The ester mixture may comprise from about 2% by weight to about 3% by weight methyl cis,cis,cis-9,12,15-octadecatrienoate (linolenic acid methyl ester/methyl linolenate).

The ester mixture may comprise from about 0.17% by weight to about 0.2% by weight methyl eicosanoate (arachidic acid methyl ester/methyl arachidate).

The ester mixture may comprise from about 0.4% by weight to about 0.6% by weight methyl cis-9-eicosenoate (gadoleic acid methyl ester/methyl gadoleate).

The ester mixture may comprise from about 0.03% by weight to about 0.07% by weight methyl docosanoate (behenic acid methyl ester/methyl behenate).

The ester mixture may comprise from about 0.04% by weight to about 0.07% by weight methyl cis-13-docosenoate (erucic acid methyl ester/methyl erucate).

The ester mixture may comprise from about 0.28% by weight to about 0.3% by weight methyl tetracosanoate (lignoceric acid methyl ester/methyl lignocerate).

The ester mixture may comprise from about 0.04% by weight to about 0.08% by weight methyl cis-15-tetracosenoate (nervonic acid methyl ester/methyl nervonate).

The composition may comprise a cetane number of from about 60 to about 65.

The composition may comprise a cold filter plugging point of from about 1° C. to about 5° C.

The composition may comprise a density of from about 865 kgm$^{-3}$ to about 875 kgm$^{-3}$.

The esters may be alkyl esters, optionally mono-alkyl esters, optionally methyl esters.

The biodiesel composition may be obtained from a mixture comprising fat, oil and/or grease. The fat, oil and/or grease may be obtained from sewage.

The composition may comprise from about 98% by weight to about 99% by weight ester mixture.

According to a fifth aspect of the invention there is provided a fuel comprising the biodiesel composition of the fourth aspect.

According to a sixth aspect of the invention there is provided a fuel blend comprising the biodiesel composition of the fourth aspect, and a petroleum diesel.

According to a seventh aspect of the invention, there is provided a biodiesel composition comprising a cetane number of from about 60 to about 65.

According to a eighth aspect of the invention, there is provided a biodiesel composition comprising a cold filter plugging point of from about 1° C. to about 5° C.

According to a ninth aspect of the invention, there is provided a biodiesel composition comprising a density of from about 865 kgm$^{-3}$ to about 875 kgm$^{-3}$.

The alternative features and different embodiments as described for the first to sixth aspects apply to the seventh to ninth aspects and each and every embodiment thereof and vice versa, mutatis mutandis.

According to a tenth aspect of the invention, there is provided a process for producing biodiesel from a mixture comprising fat, oil and/or grease obtained from sewage, said process comprising the steps of: (i) providing the mixture to a trans-esterification reaction vessel; (ii) introducing trans-esterification conditions to the trans-esterification reaction vessel; (iii) trans-esterifying the triglycerides in the mixture; and (iv) providing a first purification of the trans-esterified mixture, wherein the first purification of the trans-esterified mixture comprises spraying an aqueous solution, optionally water, onto the surface of the mixture in the trans-esterification reaction vessel, the aqueous solution percolating the mixture and facilitating the removal of impurities therefrom.

The process may comprise the further step of heating the mixture to a reaction temperature for trans-esterification.

The process may comprise the further step of maintaining the mixture at a reaction temperature for trans-esterification.

The trans-esterification reaction temperature may be between approximately 48° C. and approximately 62° C., optionally between approximately 52° C. and approximately 58° C., optionally approximately 55° C.

The amount of free fatty acids (FFAs) in the mixture before trans-esterification may be approximately 3% by weight or less.

Free fatty acid(s) are commonly referred to by the acronym FFA(s), and the terms "FFA" and "FFAs" are used herein in reference to "free fatty acid" and "free fatty acids" respectively.

The step of introducing trans-esterification conditions may comprise adding a trans-esterification catalyst, optionally base, and an alcohol, optionally methanol, to the reaction vessel.

The trans-esterification catalyst may be a methoxide or a suitable salt thereof, optionally from approximately 12% by weight to approximately 14% by weight methoxide, optionally from approximately 12.5% by weight to approximately 13% by weight methoxide.

The mass of trans-esterification catalyst used relative to the % by weight FFAs in the mixture after esterification may be from approximately 1,000 kg per % by weight FFAs to approximately 1,500 kg per % by weight FFAs, optionally from approximately 1,100 kg per % by weight FFAs to approximately 1,450 kg per % by weight FFAs.

The trans-esterification step may comprise: (i) a first trans-esterification step; and (ii) a second trans-esterification step.

In the first trans-esterification step the mass of trans-esterification catalyst used relative to the % by weight FFAs in the mixture after esterification may be from approximately 1,000 kg catalyst per % by weight FFAs to approximately 1,500 kg catalyst per % by weight FFAs, optionally from approximately 1,100 kg catalyst per % by weight FFAs to approximately 1,450 kg catalyst per % by weight FFAs.

In the second trans-esterification step the mass of trans-esterification catalyst used relative to the % by weight FFAs in the mixture after esterification may be from approximately 550 kg catalyst per % by weight FFAs to approximately 650 kg catalyst per % by weight FFAs, optionally approximately 500 kg catalyst per % by weight FFAs.

The first purification step may be carried out at a temperature of between approximately 47° C. and approximately 61° C., optionally between approximately 51° C. and approximately 57° C., optionally approximately 54° C.

The process may comprise the further step after trans-esterification of separation of a phase comprising impurities from the mixture, said separation comprising spraying an acid solution, optionally a phosphoric acid solution, onto the surface of the mixture in the trans-esterification reaction vessel, the acid solution percolating the mixture and facilitating the removal of impurities therefrom.

The separation step may be carried out at a temperature of between approximately 48° C. and approximately 62° C., optionally between approximately 52° C. and approximately 58° C., optionally approximately 55° C.

The acid solution in the separation step may be from approximately 1.0% by weight acid to approximately 1.8% by weight acid, optionally from approximately 1.2% by weight acid to approximately 1.6% by weight acid, optionally approximately 1.4% by weight acid.

The separation step may be performed before the first purification step.

The process may comprise the further step of a second purification of the trans-esterified mixture.

The second purification step may comprise spraying an acid solution, optionally a phosphoric acid solution, onto the surface of the mixture in the trans-esterification reaction vessel, the acid solution percolating the mixture and facilitating the removal of impurities therefrom.

The second purification step may be carried out at a temperature of between approximately 47° C. and approximately 61° C., optionally between approximately 51° C. and approximately 57° C., optionally approximately 54° C.

The acid solution in the second purification step may be from approximately 0.8% by weight acid to approximately 1.4% by weight acid, optionally from approximately 1.0% by weight acid to approximately 1.6% by weight acid, optionally approximately 1.2% by weight acid.

The second purification step may be performed after the first purification step.

The process may comprise the further step of a third purification of the trans-esterified mixture.

The third purification step may comprise spraying an aqueous solution, optionally water, onto the surface of the mixture in the trans-esterification reaction vessel, the aqueous solution percolating the mixture and facilitating the removal of impurities therefrom.

The third purification step may be carried out at a temperature of between approximately 47° C. and approximately 61° C., optionally between approximately 51° C. and approximately 57° C., optionally approximately 54° C.

The third purification step may be performed after the second purification step.

The process may comprise the further step of distilling the mixture after purification, said distillation process configured to remove sulphur and/or sulphur containing materials from the mixture.

The distillation step may comprise: (i) a first distillation; and (ii) a second distillation.

The distillation may be under vacuum, optionally at a pressure of from approximately 0.1 millibar (10 Pa) to approximately 3 millibar (300 Pa).

The first distillation step may comprise injecting steam at a pressure of from approximately 3.5 bar (350 kPa) to approximately 9 bar (900 kPa).

The second distillation step may comprise injecting steam at a pressure of from approximately 4.5 bar (450 kPa) to approximately 11 bar (1,100 kPa).

The impurities may be selected from one or more of group consisting of: glycerides, glycerol, methanol, water, salts, acids, bases, condensed volatile compounds and soaps.

The process may comprise the further step of removing the impurities from the mixture.

The process may comprise the further step of isolating one or more materials from the impurities, said isolated materials selected from one or more of the group consisting of: glycerides, glycerol, methanol and FFAs.

The isolated material may be reused in the process or a subsequent process for producing biodiesel.

The process may comprise the additional step of esterifying the mixture before trans-esterifying the mixture, said esterification process comprising the steps of: (i) providing at least a first portion of the mixture to at least a first esterification reaction vessel; (ii) heating the first portion of the mixture to a reaction temperature for esterification; (iii) introducing esterification conditions to the first esterification reaction vessel; (iv) stopping the heating of the first portion of the mixture; (v) recirculating the first portion of the mixture by removing it from the first esterification reaction vessel and returning it to the first esterification reaction vessel; and (vi) esterifying FFAs in the first portion of the mixture, wherein the recirculation of the first portion of the mixture is configured to maintain a reaction temperature suitable for esterification of the FFAs in the first portion of the mixture.

Optionally there is provided two or more esterification reaction vessels, said process comprising the further steps of: (i) providing at least a second portion of the mixture to at least a second esterification reaction vessel; (ii) heating the second portion of the mixture to a reaction temperature for esterification; (iii) introducing esterification conditions to the second esterification reaction vessel; (iv) stopping the heating of the second portion of the mixture; (v) recirculating the second portion of the mixture by removing it from the second esterification reaction vessel and returning it to the second esterification reaction vessel; and (vi) esterifying the FFAs in the second portion of the mixture, wherein the recirculation of the second portion of the mixture is configured to maintain a reaction temperature suitable for esterification of the FFAs in the second portion of the mixture.

The esterification of the first portion of the mixture and the esterification of the second portion of the mixture may be at least partly concurrent.

The amount of FFAs in the mixture may be reduced to approximately 3% by weight or less.

The esterification reaction temperature may be between approximately 71° C. and approximately 76° C., optionally between approximately 72° C. and approximately 75° C., optionally approximately 73.5° C.

The mixture may comprise from approximately 10% to approximately 20% by weight FFAs, optionally from approximately 10% to approximately 15% by weight FFAs, optionally from approximately 13% to approximately 15% by weight FFAs, optionally approximately 14% by weight FFAs before esterification.

Introducing esterification conditions may comprise adding an esterification catalyst, optionally an acid, and an alcohol, optionally methanol, to the reaction vessel.

The esterification catalyst may be sulphuric acid, optionally 96% sulphuric acid.

The mass of esterification catalyst used relative to the % by weight FFAs in the mixture before esterification may be from approximately 26 kg per % by weight FFAs to approximately 32 kg per % by weight FFAs.

According to an eleventh aspect of the invention there is provided a biodiesel composition obtained, obtainable or directly obtained by the process of the tenth aspect.

According to a further aspect of the invention, there is provided a fuel comprising the biodiesel composition obtained, obtainable or directly obtained by the process of the tenth aspect.

According to a further aspect of the invention, there is provided a fuel blend comprising the biodiesel composition obtained, obtainable or directly obtained by the process of the tenth aspect, and a petroleum diesel.

According to a further aspect of the invention, there is provided a fuel obtained, obtainable or directly obtained from the purified mixture of the process of the tenth aspect, the fuel optionally being biodiesel.

According to a further aspect of the invention there is provided the use of the purified mixture obtained, obtainable or directly obtained by the process of the tenth aspect in the preparation of a fuel, the fuel optionally being biodiesel.

The alternative features and different embodiments as described apply to each and every aspect and each and every embodiment thereof mutatis mutandis.

BRIEF DESCRIPTION OF THE DRAWINGS

Embodiments of the invention will now be described, by way of example only, with reference to the drawings, in which.

DETAILED DESCRIPTION

Obtaining biodiesel from sewer grease involves first purifying the sewer waste. This involves filtering the sewer waste to remove debris, and then phase separating the filtered sewer waste to minimise the aqueous phase, remove any solid particulates, and maximise the organic phase (i.e., the sewer grease fraction). This is described in more detail below under the Purification heading.

After purification, it may be necessary to reduce the free fatty acid (FFA) content of the mixture. Typically this is done using high pressure esterification as is known in the art. For example, high pressure esterification may be carried out at approximately 190° C. to 260° C. and approximately 65 bar (6.5 MPa) to 100 bar (10 MPa) in the presence of methanol.

Figure 3:
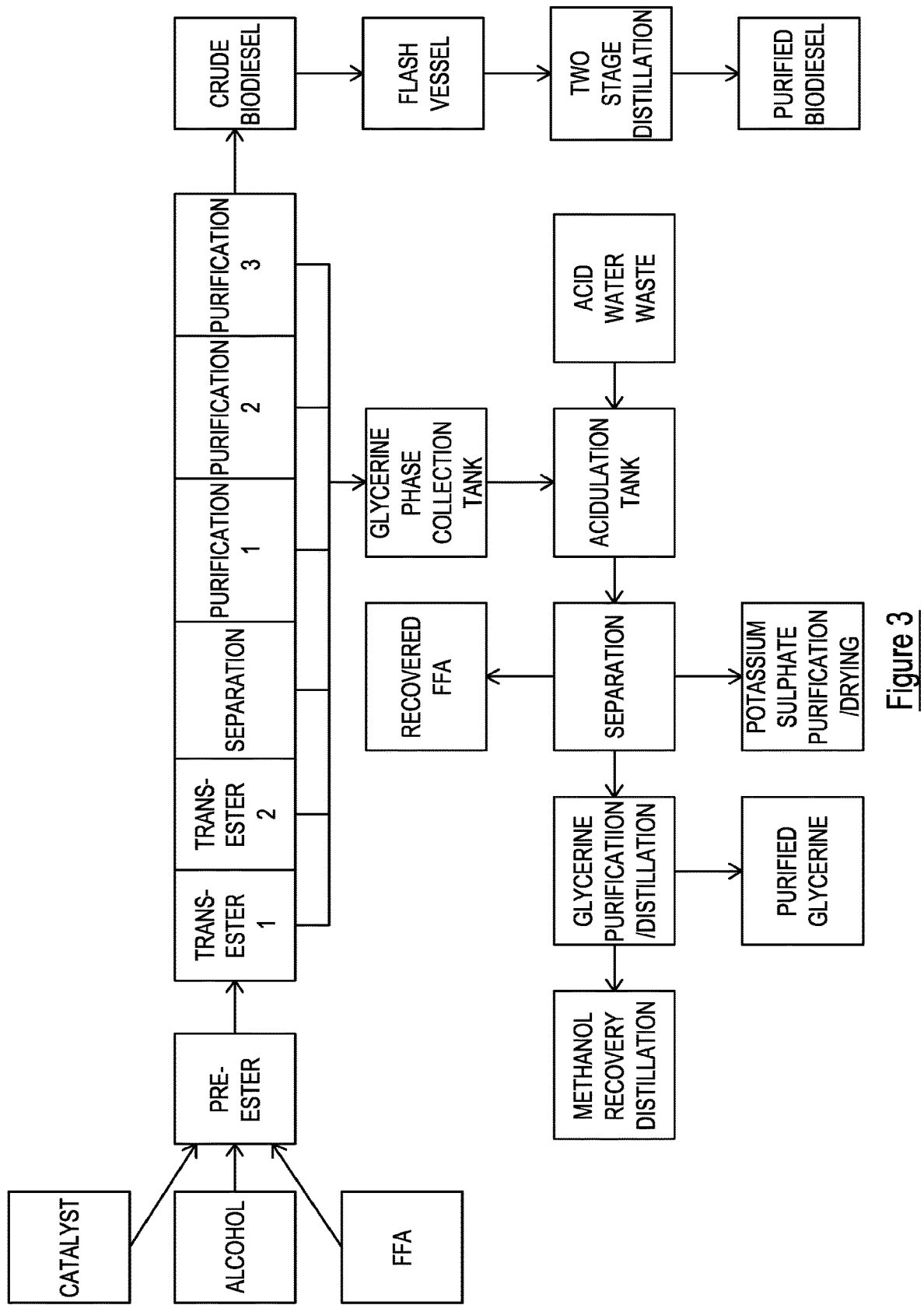
FIG. 3 is a flow diagram which illustrates a pre-esterification and trans-esterification process in accordance with one embodiment of the invention.

After purification, and optional high pressure esterification, the biodiesel production process may commence. The biodiesel production process is broken down into two areas, namely esterification (referred to as pre-esterification) and trans-esterification. The pre-esterification and trans-esterification processes as further described below under the appropriate headings, and are illustrated in the flow diagram of FIG. 3.

Purification

Figure 1:
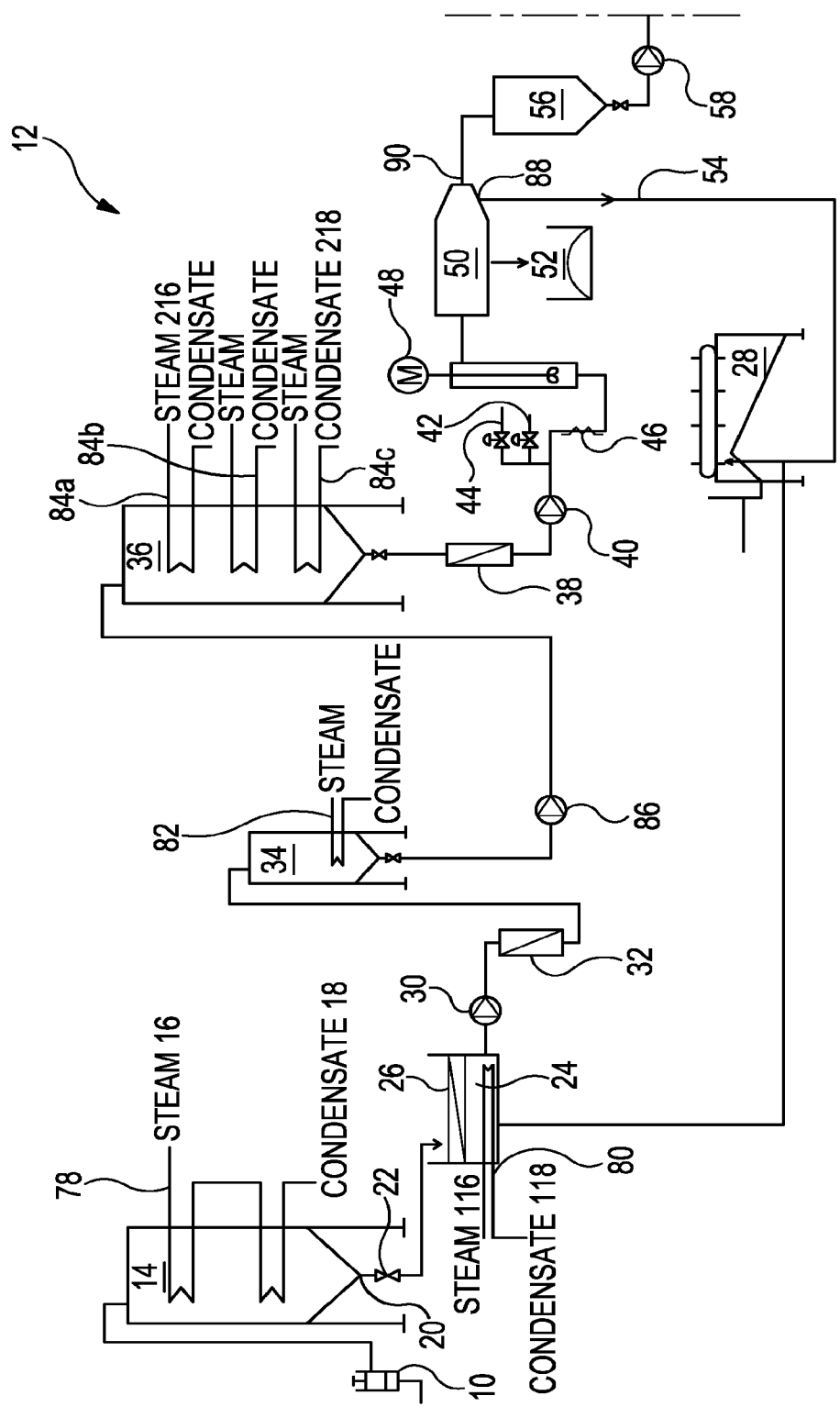
FIG. 1 is schematic diagram of a purification process.
Figure 1:
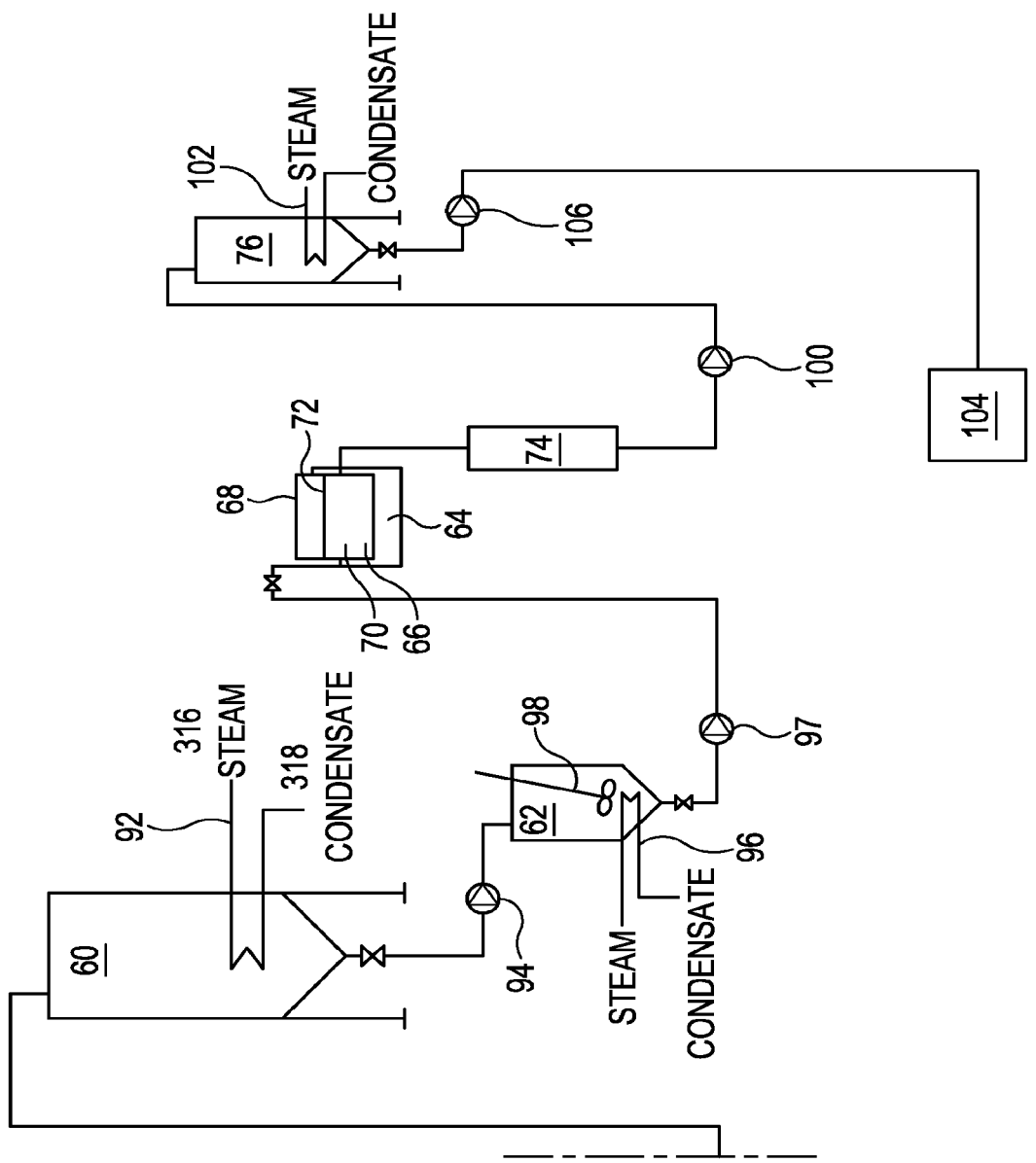

Referring to FIG. 1, the first step involves taking a fat, oil and grease mixture from a sewage treatment works (not shown) and transferring these to a tanker (not shown). The tanker then transports the mixture to a treatment plant 12. The mixture is a multi-phase mixture, comprising at least an organic (liquid) phase, an aqueous (liquid) phase and a solid phase.

The mixture is then subjected to initial heating to 60° C. using steam injection in order to make the mixture sufficiently mobile for processing (i.e., the mixture is made flowable). A range of temperatures between 55° C. and 65° C., or typically 57° C. and 63° C., can be used.

The mixture is then transferred using a piston pump 10 (VRH 250) to a reception/dewatering tank 14, where the mixture is heated to 95° C. using a double heating coil 78 (a heating device) and/or using steam injection (steam in 16, condensate out 18) for a time of approximately 5 hours, which pasteurises the mixture. The heating time may, however, be between approximately 4 hours and approximately 6 hours, or between approximately 4.5 hours and 5.5 hours. Heating to 95° C. also improves oil, water and solid separation. A range of temperatures between 90° C. and 100° C. or, typically 92° C. and 98° C., can be used. The organic phase (also referred to as the oil phase or the lipid phase), aqueous phase and solids begin to separate out in the reception/dewatering tank 14. The reception/dewatering tank 14 has an 8" (approximately 20 cm) outlet 20 to help prevent blockage when the mixture is discharged from the reception/dewatering tank 14. The flow is controlled by an 8" (approximately 20 cm) manual knife valve 22, which will cut through debris, again helping to prevent blockage of the outlet 20.

After heating, the mixture is discharged from the reception/dewatering tank 14. As the mixture from the reception/dewatering tank 14 has begun to separate, the mixture discharged is initially primarily aqueous phase and settled solids. This enters the open topped tank 24 through an integral 6 mm perforated mesh 26 which removes large particulate matter (debris). The aqueous phase is diverted to an effluent treatment facility 28 until the mixture being discharged from the reception/dewatering tank 14 changes from aqueous phase to organic phase. The solids retained by the filter mesh 26 are removed periodically throughout the process to prevent the mesh 26 from becoming blocked. The mixture has now been through a primary screening.

The melting bath/open topped tank 24 has a steam/heating coil 80 (steam in 116, condensate out 118) located in the bottom to maintain a temperature sufficient to keep the mixture in a mobile, flowable state (i.e., to prevent solidification). Any residual organic phase in the aqueous phase is recovered through a dissolved air flotation unit 28. This recovered organic phase can be introduced back into the process at a later stage, ensuring minimum losses.

A dissolved air flotation unit is a water treatment process that clarifies water or such like by the removal of suspended matter such as solids or organic liquids, such as fats, oils and greases. The removal is achieved by first reacting the mixture in the unit with a coagulant (for example, ferric or aluminium sulphate, or ferric or aluminium chloride), and then adjusting the pH to between pH 5 and pH 7 using an alkali or base such as, for example, sodium hydroxide. The resultant colloid is then removed using a polymer based flocculant ionic polyacrylamide (Millfloc™ V39™). The flocs are then removed by dissolving air in the water under pressure and then releasing the air at atmospheric pressure in a flotation tank or basin. The released air forms small bubbles which adhere to the suspended matter causing the suspended matter to float to the surface of the water where it may then be removed by a skimming device.

Referring again to FIG. 1, after primary screening, a centrifugal pump 30 is used to transfer the mixture via a 3 mm mesh inline filter 32 to a heated conical consolidation tank 34 with a heating coil 82, where further settling occurs. After settling, the aqueous phase and the solids are decanted into an appropriate waste receptacle (not shown) for disposal.

The organic phase from the consolidation tank 34 is then transferred to a heated and lagged holding tank 36 (heating by a heating coil 84*a*, 84*b*, 84*c*, steam in 216, condensate out 218), using a centrifugal pump 86, and where the mixture is held prior to further purification. The mixture from this tank 36 is drawn through a duplex inline filter 38 with a 2 mm mesh by a Waukesha™ gear pump 40 at a rate of between 1,500 and 2,500 kg per hour. During this transfer process, water and 75% by weight phosphoric acid (80 to 100 kg per hour and 1.5 to 2.5 kg per hour respectively) are injected via inlets 42 and 44 respectively into the mixture, before the mixture enters a static inline mixer 46. The acidification step alters the pH to pH 5 or less. However, the pH can usefully be between approximately pH 4.7 and approximately pH 4.8. The mixture is then heated by introducing steam at 5 to 7 bar(g) (600 to 800 kPa) into mixer 46, heating the mixture to 85° C. to 95° C. Mixing is further enhanced using a rotating mechanical mixer 48 that is situated in line, ensuring that the mixture is homogenised before being separated.

The homogenised mixture is transferred to a three phase separation unit 50, which is a counter current horizontal decanter centrifuge (Z4E-3/441 g TRICANTER®). The three phase separation unit 50 is run at a bowl speed of 3,400 RPM and a scroll speed of 12 to 14 RPM. The separated solids drop into a suitable receptacle 52 underneath the three phase separation unit 50. The aqueous phase is removed through an outlet port 88 under vacuum and is piped to the drainage system 54. Organic materials in the aqueous phase are recovered using a dissolved air flotation unit 28. The separated organic phase passes over a weir (not shown) located within the separation unit 50 and is removed through an outlet port 90 under gravity, before being piped to a buffer tank 56. The organic phase is then transferred using a positive displacement pump 58 to a heated and lagged bulk storage tank 60 equipped with a heating element 92. The separation step involves the simultaneous separation and discharge of a solid fraction, an organic liquid fraction (phase) and an aqueous liquid fraction (phase).

The three phase separation unit 50 may be used with the following settings: Bowl speed: 3,000 to 4,000 RPM; and/or Scroll speed: 10 to 20 RPM.

To ensure that the organic phase is suitable for high pressure/temperature esterification (one of the first stages in preparing the material for biodiesel production) the organic phase is subjected to a final filtration step which removes any remaining solid contaminants. The organic phase is transferred using a centrifugal pump 94 from the bulk holding tank 60 (steam in 316, condensate out 318) into a heated buffer tank 62 equipped with a heating element 96 and a mixer 98 before being pumped using positive displacement pump 97 into the sump 64 of a rotary vacuum filter 66 (ROTAVAC®). The rotary vacuum filter 66 comprises a layer (or bed) of wood flour 68 around the circumference thereof, and through which the mixture is filtered. The wood flour 68 is initially mixed with organic phase material before being drawn on the drum 70 of the rotary vacuum filter 66. The organic phase is drawn from the sump 64 through the bed 68 leaving any contamination behind. A knife 72 cuts continually into the bed 68 exposing a new filter area, this ensures that an optimum filtration rate is maintained. The mixture is maintained at a temperature of 80° C. during the filtration process. However, the temperature may be between approximately 75° C. and approximately 85° C., or between approximately 72° C. and approximately 83° C., or between 65° C. and 85° C.

The rotary vacuum filter 66 may be used with the following settings: Cutting rate: 100 to 200 micrometers per revolution; Wood flour type/grade: cellulose fibre 110; and/or Rotational speed: 1 to 2.5 RPM.

Once filtered, the purified mixture is drawn into the filtrate tank 74 for storage. The purified mixture is then transferred using a positive displacement pump 100 to a final tank 76, equipped with a heating coil 102 before being transferred to a high pressure esterification plant 104 by way of a pump 106. This plant 104 prepares the purified mixture for further processing, such as the biodiesel formation process.

The purified mixture obtained is subject to high pressure esterification, which is a well-known process. In this instance, the high pressure esterification is carried out between 190° C. to 260° C. and approximately 65 bar (6.5 MPa) to 100 bar (10 MPa) in the presence of methanol.

The pre-esterification and trans-esterification processes described below are based on approximately 38 tonnes of feedstock (including recovered FFAs) being used.

Pre-Esterification

Pre-esterification is a preconditioning step that produces useable oil for the trans-esterification process. It involves the catalysed esterification of free fatty acids (FFAs) with an alcohol to provide a fatty acid ester.

Figure 2:
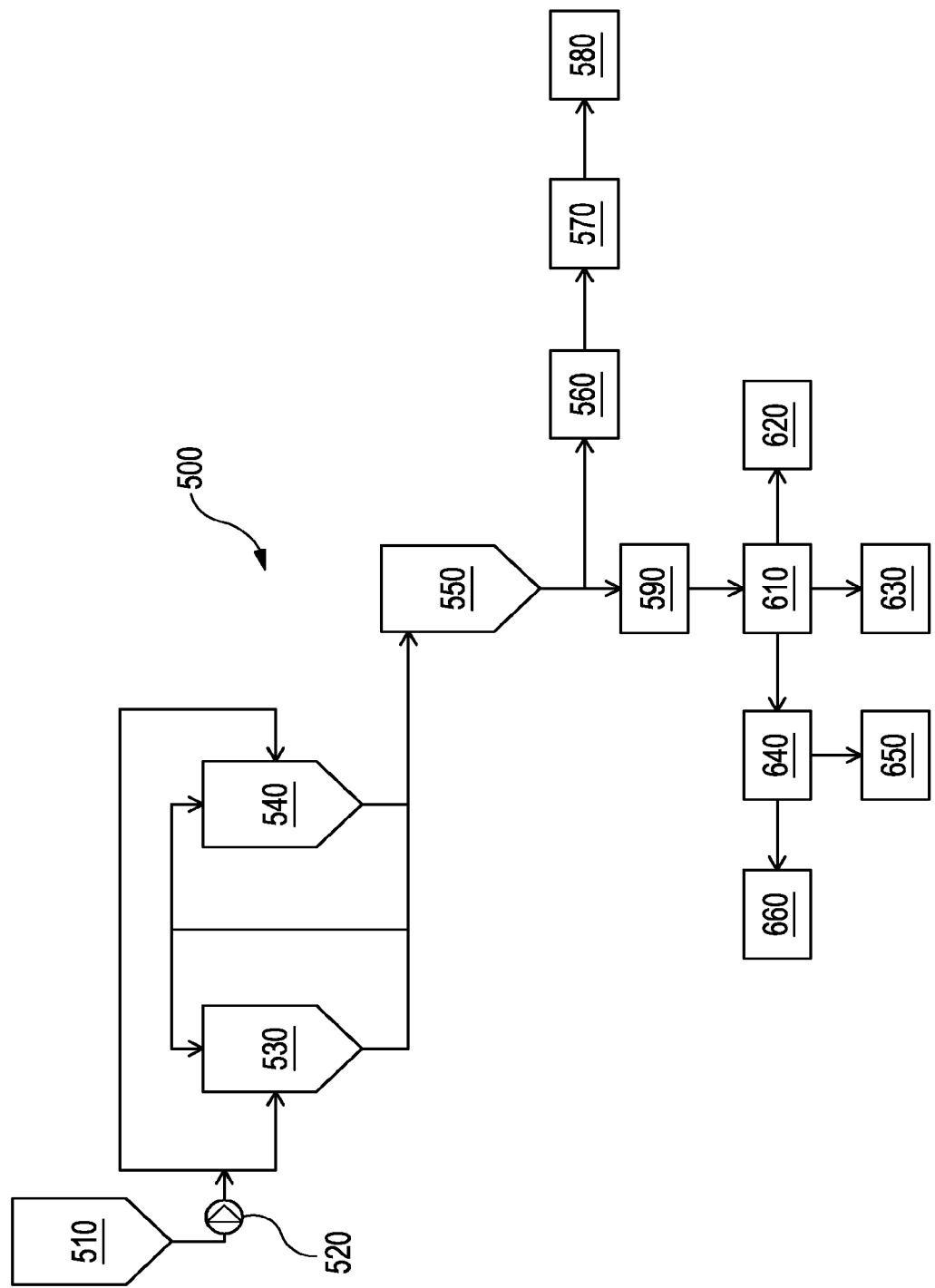
FIG. 2 is schematic diagram of a pre-esterification and trans-esterification process in accordance with one embodiment of the invention.

Referring to FIG. 2, there is shown at 500 an apparatus for producing biodiesel. The apparatus comprises a feedstock tank 510 from which sewer grease, which comprises FFAs, and recovered FFAs from the by-product stream of an earlier biodiesel production process, are pumped via pump 520 into a first pre-esterification reactor 530. The total amount of FFAs in the feedstock is typically between 10% by weight and 20% by weight. Under normal operation conditions, the combined amount of FFAs (i.e., when tallow and recovered FFAs are combined) is 10% by weight to 15% by weight, but may also be 13% by weight to 15% by weight. In one embodiment, the total amount of FFAs in the feedstock is 14% by weight.

100 kg of methanol (an alcohol) per tonne of feedstock is then added to the feedstock in the first pre-esterification reactor 530, followed by the addition of 96% by weight sulphuric acid (an esterification catalyst). A range of methanol can be used, varying between 80 kg and 120 kg per tonne of feedstock, and usually between 90 kg and 110 kg per tonne of feedstock. The so-formed mixture is then heated for at least 90 minutes with agitation to a reaction temperature of approximately 73.5° C. The temperature can be between approximately 71° C. and 76° C., and is typically is from between 72° C. and 75° C.

Once the reaction temperature has been reached in the first pre-esterification reactor 530, the mixture is removed from and then returned to the first pre-esterification reactor 530 by recirculation of the mixture such that the reaction temperature is maintained. The recirculation and reaction continues with agitation for approximately 150 minutes, which ensures that the reaction is complete. This so-formed mixture is then allowed to settle for 90 minutes before the water phase is removed.

Once the reaction temperature is reached in the first pre-esterification reactor 530, the feedstock is diverted to a second pre-esterification reactor 540.

100 kg of methanol (an alcohol) per tonne of feedstock is then added to the feedstock in the second pre-esterification reactor 540, followed by the addition of 96% by weight sulphuric acid (an esterification catalyst). A range of methanol can be used, varying between 80 kg and 120 kg per tonne of feedstock, and usually between 90 kg and 110 kg per tonne of feedstock. The so-formed mixture is then heated for at least 90 minutes with agitation to a reaction temperature of approximately 73.5° C. The temperature can be between approximately 71° C. and 76° C., and is typically is from between 72° C. and 75° C.

Once the reaction temperature has been reached in the second pre-esterification reactor 540, the mixture is removed from and then returned to the second pre-esterification reactor 540 by recirculation of the mixture such that the reaction temperature is maintained. The recirculation and reaction continues with agitation for approximately 150 minutes, which ensures that the reaction is complete. This so-formed mixture is then allowed to settle for 90 minutes before the water phase is removed.

The amount of pre-esterification catalyst used is from about 26 kg catalyst per % by weight FFAs to about 32 kg catalyst per % by weight FFAs.

The quality of the feedstock may deviate on a day to day basis, which can have a significant impact on the following steps of the biodiesel production process to the extent that in prior known processes such steps may not be viable. For example, if too many impurities are present this can prevent different phases from being separated and/or this can lead to a very poor quality end product.

Thus, fluctuations in FFA content must be taken into account to establish the amount of catalyst that is required to achieve a feedstock suitable for further processing (i.e., suitable for trans-esterification). A suitable endpoint may be when the total amount of FFAs in the mixture is reduced to 3% by weight or less. The inventors have found that a range of pre-esterification catalyst of from about 26 kg catalyst per % by weight FFAs to about 32 kg catalyst per % by weight FFAs enables a successful pre-esterification to take place.

The pre-esterification process outlined above enables two pre-esterification reactions to take place at least partly concurrently. In particular, once the contents of a pre-esterification reactor reach the reaction temperature, the heat input is removed. The contents of the pre-esterification reactor are then recirculated, the residual heat generated by the reaction enabling the reaction to continue to completion without further external heat being applied. Removing the heat input from one pre-esterification reactor enables a further reaction in another separate pre-esterification reactor to be initiated almost immediately. These improvements reduce the time taken for the pre-esterification process by at least 120 minutes, as compared with using only one pre-esterification reactor of equivalent size. Thus, the process outlined provides a significant improvement in the speed of throughput. Furthermore, the process outlined uses less energy than known pre-esterification processes, due to the use of residual heat of reaction and recirculation of the reaction mixture to maintain the reaction temperature.

Trans-Esterification

The trans-esterification process exchanges the R group on an ester for the R group from an alcohol. In the biodiesel production process it is used to convert triglycerides to fatty acid methyl esters.

Referring once more to FIG. 2, the mixture from the pre-esterification reactors 530, 540 is transferred to a trans-esterification reactor (reaction vessel) 550. The mixture in the trans-esterification reactor 550 is agitated, and recovered methyl ester is added. The recovered methyl ester is obtained later in the process from the separation and purification of the by-products.

2,900 kg of potassium methoxide and 2,500 kg of methanol are added to the mixture in the trans-esterification reactor 550, and the reaction temperature is adjusted to approximately 55° C. The amount of methanol may vary between approximately 2,000 kg and 3,000 kg. The amount of potassium methoxide used above is based on 2% by weight of FFAs in the mixture. However the amount used can be between 1,100 kg per % by weight of FFA and 1,500 kg per % by weight of FFA, typically 1,150 kg per % by weight of FFA and 1,450 kg per % by weight of FFA. Also, the reaction temperature is a reaction temperature for trans-esterification and can be between approximately 48° C. and approximately 62° C., and is typically between approximately 52° C. and approximately 58° C.

Where the catalyst is methoxide in methanol, the amount of methoxide is 12% to 14% by weight methoxide, typically 12.5% by weight to 13% by weight methoxide. The conditions described above are trans-esterification conditions and, specifically, are used to trans-esterify triglycerides in the mixture.

Using the amounts of potassium methoxide noted ensures that the reaction mechanism is driven to completion i.e., methyl ester is formed and glycerol is removed. Whilst in this example potassium methoxide catalyst and methanol in excess is used, other suitable methoxides can be used such as, for example, sodium methoxide.

A second trans-esterification is then carried out in the trans-esterification reactor 550 using a smaller quantity of potassium methoxide catalyst (approximately 600 kg) and methanol (approximately 1,000 kg).

The amount of potassium methoxide catalyst may be between approximately 550 kg to approximately 650 kg. The amount of methanol may be between approximately 900 kg to approximately 1,100 kg. The second trans-esterification reaction ensures that substantially all of the triglycerides in the mixture are converted to esters, and that substantially all of the glycerol is removed.

The reaction temperature is adjusted to approximately 55° C., and the reaction is run for around 300 minutes. The reaction temperature is a reaction temperature for trans-esterification and can be between approximately 48° C. and approximately 62° C., and is typically between approximately 52° C. and approximately 58° C.

An optional separation step can be used to aid settling, particularly if the aqueous and non-aqueous phases of the mixture prove difficult or very time-consuming to separate. The separation step involves spraying an aqueous solution comprising 1,000 kg of recycled water and 10 kg to 18 kg of 75% by weight phosphoric acid onto the surface of the mixture in the trans-esterification reactor 550 at a temperature of approximately 70° C. The temperature may be between approximately 60° C. and approximately 80° C. The acid solution percolates through the mixture and the contents of the trans-esterification reactor 550 are allowed to settle for 60 minutes before the so-formed aqueous phase is discharged into a glycerine (aqueous) phase collection tank 590. This process removes impurities and better enables separation of soaps.

Based on the amounts stated above, the acid solution used in the separation step is 1.0% by weight acid to 1.8% by weight acid, but can be from 1.2% by weight acid to 1.6% by weight acid, typically 1.4% by weight acid.

The mixture, still in the trans-esterification tank 550, is then subjected to a first purification (washing) step. The first purification step involves adding approximately 500 kg of water to the mixture, and mechanically agitating the mixture combined with the water, before allowing to settle for approximately 100 minutes. The amount of water used may vary between 400 kg and 600 kg. An aqueous solution comprising 250 kg (150 kg to 350 kg can be used) of recycled water at a temperature of 70° C. (a temperature of 60° C. to 80° C. can be used) is then sprayed onto the surface of the mixture in the trans-esterification reactor 550 before allowing to settle for approximately 140 minutes. The water percolates through the mixture and the contents of the trans-esterification reactor 550 are allowed to settle for 60 minutes before the so-formed aqueous phase is discharged into a glycerine (aqueous) phase collection tank 590.

The mixture, still in the trans-esterification tank 550, is then subjected to a second purification (washing) step. The second purification involves spraying an aqueous solution comprising 1,000 kg of heated (recycled) water and 14 kg of 75% by weight phosphoric acid onto the surface of the mixture in the trans-esterification reactor 550. The temperature of the solution is 70° C. (a temperature of 60° C. to 80° C. can be used). The acid solution percolates through the mixture and the contents of the trans-esterification reactor 550 are allowed to settle for 60 minutes before the so-formed aqueous phase is discharged into a glycerine (aqueous) phase collection tank 590. This process removes impurities and neutralises residual potassium soaps.

Based on the amounts stated above, the acid solution used in the second purification (washing) step is 0.8% by weight acid to 1.6% by weight acid, but can be from 1.0% by weight acid to 1.4% by weight acid, typically 1.2% by weight acid.

A further (third) purification (washing) step is applied to the mixture in the trans-esterification reactor 550. The third purification step involves spraying an aqueous solution comprising 500 to 1,000 kg of recycled water at a temperature of 70° C. (a temperature of 60° C. to 80° C. can be used) onto the surface of the mixture in the trans-esterification reactor 550. The water percolates through the mixture and the contents of the trans-esterification reactor 550 are allowed to settle for 60 minutes before the so-formed aqueous phase is discharged into a glycerine (aqueous) phase collection tank 590. This third purification process ensures that the vast majority of impurities, free glycerides and soaps are removed prior to the non-aqueous phase of the mixture (which is now crude biodiesel) entering a flash vessel 560.

The percolation of the aqueous solutions through the mixture in the trans-esterification reactor 550 facilitates the removal of impurities from the mixture. The impurities removed include, for example, the following: glycerides, glycerol, methanol, water, salts, acids, bases, condensed volatile compounds and soaps.

Depending on the feedstock material used, some or all of the separation/purification steps described above are required. The separation/purification steps ensure that the process is not unduly lengthy. For example, in prior known processes settling problems may be encountered, which can then lead to excessive waiting times for the separation of the aqueous and non-aqueous phases. The separation step described above helps to overcome such settling problems should they occur. Overall, the separation/purification (washing) steps described can reduce by around 5 hours the time taken to obtain crude biodiesel from the trans-esterification process.

The crude biodiesel mixture obtained from the separation/purification steps is provided to the flash vessel 560, where the crude biodiesel (fatty acid methyl ester mixture) is steam treated (steam injection) under vacuum to remove water, volatile compounds, and free glycerides, all of which may impact on the final quality or the operation of the vacuum system in the distillation step which follows.

From the flash vessel 560, the mixture is transferred to a distillation apparatus 570, where remaining impurities (such as glycerides, water and sulphur or sulphur containing materials) are removed under vacuum, the pressure being set to approximately 0.1 millibar (10 Pa) to approximately 3 millibar (300 Pa).

The distillation takes place is two stages. The first stage has the following conditions. Steam is injected at a pressure of from approximately 3.5 bar (350 kPa) to approximately 9 bar (900 kPa).

The second stage has the following conditions. Steam is injected at a pressure of from approximately 4.5 bar (450 kPa) to approximately 11 bar (1,100 kPa).

The product produced from the distillation apparatus is purified biodiesel, which is transferred to biodiesel tank 580.

The purified biodiesel may be used as a fuel, or may be blended with other products to produce a fuel.

Impurities are periodically removed from the process. For example, the aqueous (glycerine containing) phase from the trans-esterification is periodically separated into the glycerine phase tank 590. This aqueous phase may contain glycerol, methanol, water, salts, acids, bases, condensed volatile compounds and soaps, for example.

The aqueous phase is further transferred to an acidulation tank 610 to which acid water waste is added. The aqueous phase is then separated into recovered FFAs (recovered FFA tank 620), potassium sulphate (potassium sulphate tank 630) and glycerine/methanol (glycerine/methanol tank 640). The glycerine methanol is further separated into purified glycerine (purified glycerine tank 650) and recovered methanol (recovered methanol tank 660). The materials isolated from the impurities can be reused in a subsequent process for producing biodiesel.

EXAMPLES

Several aliquots of sewer grease derived biodiesel as prepared using the above process were analysed for their chemical constituents and tested for their physical properties. In particular, the methyl ester content was analysed. The results are illustrated below in Table 1 and Table 2.

TABLE 1

Physical/Chemical Properties of Sewer Grease Derived Biodiesel

| Fuel Parameter | Example 1 | Example 2 | Example 3 |
|---|---|---|---|
| Ester Content (% by weight) | 99 | 98 | 98.5 |
| Iodine Number | 65 | 75 | 70 |
| Cetane Number | 60 | 65 | 62.5 |
| Cold Filter Pugging Point (° C.) | 5 | 1 | 3 |
| Density (kgm$^{-3}$) | 875 | 865 | 870 |
| Kinematic Viscosity (mm$^2$s$^{-1}$) | 4.2 | 4.6 | 4.4 |
| Mono-glycerides (% by weight) | 0.1065 | 0.1167 | 0.1116 |
| Saturated monoglycerides (% by weight) | 0.0376 | 0.0463 | 0.0419 |

The physical and chemical properties of the sewer grease derived biodiesel, and the tallow and used cooking oil derived biodiesels, were determined in accordance with available European Standards ("EN") or International Petroleum Test Methods ("IP"). The following standards and test methods were used: i. Determining ester content: EN 14103, ii. Determining the iodine number: EN 14111, iii. Determining cetane number: IP 498, iv. Determining cold filter plugging point: EN 116, v. Determining density: EN ISO 3675, vi. Determining the kinematic viscosity: ISO 3104, and vii. Determining the glyceride content: EN 14105.

TABLE 2

Methyl Esters in Sewer Grease Derived Biodiesel (% by weight)

| Methyl Ester | Example 1 | Example 2 | Average |
|---|---|---|---|
| methyl octadecanoate (stearic acid methyl ester/methyl stearate) | 7 | 10.5 | 8.75 |
| methyl heptadacanoate (heptadecanoic acid methyl ester/methyl margarate) | 0.5 | 1.9 | 1.2 |
| weight methyl tetradecanoate (myristic acid methyl ester/methyl myristate) | 2.9 | 2.4 | 2.65 |
| methyl hexadecancate (palmitic acid methyl ester/methyl palmitate) | 22.7 | 24.4 | 23.55 |
| methyl cis-9-hexadecenoate (palmitoleic acid methyl ester/methyl) palmitoleate) | 1.5 | 2.1 | 1.8 |
| methyl cis-9-octadecenoate (oleic acid methyl ester/methyl oleate) | 39 | 41 | 40 |
| methyl cis,cis-9,12-octadecadienoate (linoleic acid methyl ester/methyl linoleate) | 20 | 15 | 17.5 |
| methyl cis,cis,cis-9,12,15-octadecatrienoate (linolenic acid methyl ester/methyl linolenate) | 3 | 2 | 2.5 |
| methyl eicosanoate (arachidic acid methyl ester/methyl arachidate) | 0.17 | 0.2 | 0.185 |
| methyl cis-9-eicosenoate (gadoleic acid methyl ester/methyl gadoleate) | 0.6 | 0.4 | 0.5 |
| methyl docosanoate (behenic acid methyl ester/methyl behenate) | 0.07 | 0.03 | 0.5 |
| methyl cis-13-docosenoate (erucic acid methyl ester/methyl erucate) | 0.04 | 0.07 | 0.55 |
| methyl tetracosanoate (lignoceric acid methyl ester/methyl lignocerate) | 0.28 | 0.3 | 0.29 |
| methyl cis-15-tetracosenoate (nervonic acid methyl ester/methyl nervonate) | 0.04 | 0.08 | 0.06 |

As noted above, the ester content of the sewer grease derived biodiesel (and the tallow and used cooking oil derived biodiesels) was determined using European Standard EN 14103.

The sewer grease derived biodiesel was compared to other samples of biodiesel that were prepared from animal fat (tallow) or used cooking oil (UCO). The results are illustrated in Table 3 and Table 4.

TABLE 3

Physical Properties of Biodiesel Derived from Sewer Grease (SG), Tallow and Used Cooking Oil (UCO)

| Fuel Parameter | SG | Tallow | UCO |
| --- | --- | --- | --- |
| Ester Content (% by weight) | 98.5 | 99.6 | 99.1 |
| Iodine Number | 70 | 44 | 73 |
| Cetane Number | 62.5 | 59.9 | 56.7 |
| Cold Filter Pugging Point (° C.) | 3 | 11 | 6 |
| Density (kgm$^{-3}$) | 870 | 878 | 877 |
| Kinematic Viscosity (mm$^2$s$^{-1}$) | 4.4 | 4.6 | 4.4 |

TABLE 4

Methyl Esters in Biodiesel Derived from Sewer Grease (SG), Tallow and Used Cooking Oil (UCO) (% by weight)

| Methyl Ester | SG | Tallow | UCO |
| --- | --- | --- | --- |
| methyl octadecancate (stearic acid methyl ester/methyl stearate) | 8.75 | 19.11 | 11.41 |
| methyl heptadecanoate (heptadecanoic acid methyl ester/methyl margarate) | 1.2 | 5.9 | 3.5 |
| weight methyl tetradecanoate (myristic acid methyl ester/methyl myristate) | 2.65 | 2.64 | 1.53 |
| methyl hexadecanoate (palmitic acid methyl ester/methyl palmitate) | 23.55 | 24.75 | 20.02 |
| methyl cis-9-hexadecenoate (palmitoleic acid methyl ester/methyl palmitoleate) | 1.8 | 2.45 | 1.29 |
| methyl cis-9-octadecenoate (oleic acid methyl ester/methyl oleate) | 40 | 36.03 | 40.25 |
| methyl cis,cis-9,12-octadecadienoate (linoleic acid methyl ester/methyl linoleate) | 17.5 | 6.42 | 18.42 |
| methyl cis, cis, cis-9,12,15-octadecatrienoate (linolenic acid methyl ester/methyl linolenate) | 2.5 | 1.02 | 2.7 |
| methyl eicosancate (arachidic acid methyl ester/methyl arachidate) | 0.185 | 0.18 | 0.25 |
| methyl cis-9-eicosenoate (gadoleic acid methyl ester/methyl gadoleate) | 0.5 | 0.24 | 0.32 |
| methyl docosanoate (behenic acid methyl ester/methyl behenate) | 0.5 | 0.11 | 0.04 |
| methyl cis-13-docosenoate (erucic acid methyl ester/methyl erucate) | 0.55 | 0.19 | 0.07 |
| methyl tetracosanoate (lignoceric acid methyl ester/methyl lignocerate) | 0.29 | 0.2 | 0.025 |
| methyl cis-15-tetracosenoate (nervonic acid methyl ester/methyl nervonate) | 0.06 | 0.15 | 0.06 |

In further examples, the biodiesel of the present invention is mixed with petroleum derived diesel to provide a fuel blend. Examples are given in Table 5.

TABLE 5

Fuel Blends Comprising Sewer Grease (SG) Derived Biodiesel and Petroleum Diesel (% by volume)

| Blend | SG Biodiesel (% by volume) | Petroleum Diesel (% by volume) |
| --- | --- | --- |
| B5 | 5 | 95 |
| B10 | 10 | 90 |
| B15 | 15 | 85 |
| B20 | 20 | 80 |
| B25 | 25 | 75 |
| B30 | 30 | 70 |
| B35 | 35 | 65 |
| B40 | 40 | 60 |
| B45 | 45 | 55 |
| B50 | 50 | 50 |
| B55 | 55 | 45 |
| B60 | 60 | 40 |
| B65 | 65 | 35 |
| B70 | 70 | 30 |
| B75 | 75 | 25 |
| B80 | 80 | 20 |
| B85 | 85 | 15 |
| B90 | 90 | 10 |
| B95 | 95 | 5 |

The biodiesel derived from sewer grease is at least as good as currently available biodiesels and, in many respects, offers a number of potential advantages over biodiesel products currently on the market. For example, the biodiesel composition of the present invention has a relatively high cetane number. As previously discussed, the cetane number is an important characteristic that indicates the ignition quality of diesel fuels. Higher cetane numbers signify only a short delay between fuel injection and ignition, which ensures a good cold start and smooth running of an engine. Fuels with a low cetane number tend to cause "knocking" and show increased gaseous and particulate exhaust emissions due to incomplete combustion. The current minimum cetane number for a diesel fuel is 51.

Cold filter plugging point is the temperature at which a biodiesel will no longer pass through a certain grade of filter. A high cold filter plugging point can prevent a fuel from being used at lower temperatures. Surprisingly, the biodiesel composition of the present invention has a comparatively low cold filter plugging point, which is particularly unusual for a biodiesel having a relatively high cetane number. For example, tallow derived biodiesel has a relatively high cetane number, but also has a relatively high cold filter plugging point, which means that tallow derived biodiesel may not always be suitable for use in colder conditions. Thus, the relatively low cold filter plugging point, and the relatively high cetane number of the biodiesel of the present invention is unusual, unexpected and advantageous. Without wishing to be bound by theory, it is thought that the cold filter plugging point can be attributed to the ester profile of a biodiesel fuel.

In addition to the above, the density of the biodiesel composition of the present invention is relatively low. This is advantageous as it enables more biodiesel to be added to fuel blends that have a maximum allowed density. For example, often density limits are placed on blended fuels (i.e., fuels that contain both biodiesel and petroleum diesel). These density limits are based on the weighted average of the biodiesel and the petroleum diesel. In such circumstances, the lower the density of the biodiesel, then the greater the volume of biodiesel that can be added whilst still remaining within the set density limits.

Without wishing to be bound by theory, it is thought that the unique profile of the biodiesel composition derived from sewer grease provides these advantageous properties. In particular, and as can be seen from Tables 1 and 3, the biodiesel composition derived from sewer grease has a lower amount of methyl octadecanoate (stearic acid methyl ester/methyl stearate) than biodiesel obtained from tallow or used cooking oil. Again, without wishing to be bound by theory, it is believed that this may provide the unexpected and beneficial effects observed and described above. In particular, it is unusual and unexpected to have a relatively low amount of methyl octadecanoate (stearic acid methyl ester/methyl stearate) and a relatively high cetane number.

Again, without wishing to be bound by theory, another noted difference between the biodiesel composition derived from sewer grease and the biodiesel obtained from tallow or used cooking oil is the decreased amount of methyl heptadecanoate (heptadecanoic acid methyl ester/methyl margarate) in the biodiesel composition derived from sewer grease. Further differences between the compositions are apparent from Tables 1 and 3 in particular.

A further advantage of the biodiesel composition of the present invention is that it provides a biodiesel that is useable as a fuel and/or as part of a fuel blend, and that is derived from a starting material that would otherwise be a waste material. This is the case irrespective of whether the biodiesel of the present invention has improved physical properties over known biodiesels. For example, if the biodiesel of the present invention was identical or similar in physical properties to known biodiesels, it would still be advantageous given the impurity and low cost of the starting material.

The improved processes as described herein enable the use of impure and poor quality feedstocks to produce high quality biodiesel. To date, it has been otherwise impracticable to use such feedstocks as a source of fats and oils (and greases) for producing fuels such as biodiesel.

In addition, the improved processes as described herein enable a reduction in the throughput time for the production of biodiesel from a feedstock. This results in an increased amount of biodiesel production, which is of benefit. For example, the present inventors have found that their improved processes enable the production of biodiesel in approximately 7 to 8 hours less than the time taken using existing processes. For the present facility used by the inventors, this represents an additional 38 tonnes of biodiesel produced in a 24 hour period.

While this invention has been described with reference to the sample embodiments thereof, it will be appreciated by those of ordinary skill in the art that modifications can be made to the structure and elements of the invention without departing from the spirit and scope of the invention as a whole.

What is claimed is:

1. A biodiesel composition comprising a mixture of esters, wherein the ester mixture comprises from 7% by weight to 10.5% by weight methyl octadecanoate, and from 39% by weight to 41% by weight methyl cis-9-octadecenoate, and from 0.4% by weight to 0.6% by weight methyl cis-9-eicosenoate.

2. A biodiesel composition as claimed in claim 1, wherein the ester mixture comprises from 0.5% by weight to 1.9% by weight methyl heptadecanoate.

3. A biodiesel composition as claimed in claim 1, wherein the ester mixture comprises from 2.4% by weight to 2.9% by weight methyl tetradecanoate.

4. A biodiesel composition as claimed in claim 1, wherein the ester mixture comprises from 22.7% by weight to 24.4% by weight methyl hexadecanoate.

5. A biodiesel composition as claimed in claim 1, wherein the ester mixture comprises from 1.5% by weight to 2.1% by weight methyl cis-9-hexadecenoate.

6. A biodiesel composition as claimed in claim 1, wherein the ester mixture comprises from 15% by weight to 20% by weight methyl cis,cis-9,12-octadecadienoate.

7. A biodiesel composition as claimed in claim 1, wherein the ester mixture comprises from 2% by weight to 3% by weight methyl cis,cis,cis-9,12,15-octadecatrienoate.

8. A biodiesel composition as claimed in claim 1, wherein the ester mixture comprises from 0.17% by weight to 0.2% by weight methyl eicosanoate.

9. A biodiesel composition as claimed in claim 1, wherein the ester mixture comprises from 0.03% by weight to 0.07% by weight methyl docosanoate.

10. A biodiesel composition as claimed in claim 1, wherein the ester mixture comprises from 0.04% by weight to 0.07% by weight methyl cis-13-docosenoate.

11. A biodiesel composition as claimed in claim 1, wherein the ester mixture comprises from 0.28% by weight to 0.3% by weight methyl tetracosanoate.

12. A biodiesel composition as claimed in claim 1, wherein the ester mixture comprises from 0.04% by weight to 0.08% by weight methyl cis-15-tetracosenoate.

13. A biodiesel composition as claimed in claim 1, wherein the composition comprises a cetane number of from 60 to 65.

14. A biodiesel composition as claimed in claim 1, wherein the composition comprises a cold filter plugging point of from 1° C. to 5° C.

15. A biodiesel composition as claimed in claim 1, wherein the composition comprises a density of from 865 kgm-3 to 875 kgm-3.

16. A biodiesel composition as claimed in claim 1, wherein the esters are alkyl esters.

17. A biodiesel composition as claimed in claim 1, wherein the biodiesel composition is obtained from a mixture comprising fat, oil and/or grease.

18. A biodiesel composition as claimed in claim 17, wherein the fat, oil and/or grease is obtained from sewage.

19. A biodiesel composition as claimed in claim 1, wherein the composition comprises from 98% by weight to 99% by weight ester mixture.

20. A fuel comprising from 5% by volume to 95% by volume of the biodiesel composition of claim 1.

21. A fuel blend comprising from 5% by volume to 95% by volume of the biodiesel composition of claim 1 and from 5% by volume to 95% by volume of a petroleum diesel.

* * * * *